(12) United States Patent
Miyake et al.

(10) Patent No.: US 11,142,735 B2
(45) Date of Patent: Oct. 12, 2021

(54) CELL TREATMENT CONTAINER AND CELL TREATMENT DEVICE

(71) Applicant: Shimadzu Corporation, Kyoto (JP)

(72) Inventors: Chikara Miyake, Kyoto (JP); Masaki Kanai, Kyoto (JP); Yoichi Fujiyama, Kyoto (JP); Satoshi Kuramoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 196 days.

(21) Appl. No.: 16/712,238

(22) Filed: Dec. 12, 2019

(65) Prior Publication Data

US 2020/0224138 A1      Jul. 16, 2020

(30) Foreign Application Priority Data

Jan. 15, 2019   (JP) ............................. JP2019-004685

(51) Int. Cl.
*C12M 3/06*  (2006.01)
*C12M 1/00*  (2006.01)
*B01L 3/00*  (2006.01)

(52) U.S. Cl.
CPC ....... *C12M 23/16* (2013.01); *B01L 3/502753* (2013.01); *C12M 27/18* (2013.01); *C12M 29/00* (2013.01); *C12M 29/04* (2013.01); *B01L 2300/0861* (2013.01); *B01L 2400/086* (2013.01)

(58) Field of Classification Search
CPC ...... C12M 23/16; C12M 27/18; C12M 29/00; C12M 29/10; C12M 35/08; C12M 41/44; B01L 3/502753; B01L 2300/0861; B01L 2300/0681; B01L 2200/0647; B01L 2400/086

See application file for complete search history.

(56) References Cited

U.S. PATENT DOCUMENTS 8,980,624 B2 *   3/2015  Wu ........................ C12M 29/14
                                                          435/297.1

OTHER PUBLICATIONS

Andersson et al., "Micromachined Flow-Through Filter-Chamber for Solid Phase DNA Analysis", Micro Total Analysis Systems 2000, p. 473-476 (2000).

\* cited by examiner

*Primary Examiner* — Michael L Hobbs
(74) *Attorney, Agent, or Firm* — Muir Patent Law, PLLC

(57) ABSTRACT

To provide a cell treatment container, including: a first member having a flow path in which a cell suspension including a liquid and cells dispersed in the liquid flows through, the flow path formed on a surface of the first member; a second member arranged to face the surface of the first member; and a damming formed in one or both of the first member and the second member, in which the damming is provided with a protrusion part protruding from the first member into the flow path to form a gap for allowing the liquid in the cell suspension to pass through the gap and for damming up the cells in the cell suspension, and a pillar extending from the protrusion part at a first end and being joined to the second member at a second end.

9 Claims, 8 Drawing Sheets

CELL TREATMENT CONTAINER AND CELL TREATMENT DEVICE

INCORPORATION BY REFERENCE

The present application claims priority under 35 U.S.C. § 119 to Japanese Patent Application No. 2019-004685 filed on Jan. 15, 2019. The content of the applications is incorporated herein by reference in its entirety.

BACKGROUND

Technical Field

The present invention relates to a cell treatment container and a cell treatment device.

Related Art

Conventionally, as a cell treatment container, a container in which multiple pillars are arranged in a microchannel has been proposed. The multiple pillars are arranged by spacing apart from each other so as to allow a liquid to pass through the multiple pillars and to dam up cells (see Helene Andersson et al., "MICROMACHINED FLOW-THROUGH FILTER-CHAMBER FOR SOLID PHASE DNA ANALYSIS", Micro Total Analysis Systems 2000, p. 473-476).

In a cell treatment container, a cell suspension in which cells have been dispersed in a liquid is distributed through a flow path, and the cells are dammed up and inoculated in a damming. Further, the cell treatment container is used for culturing cells with the culture environment kept constant (perfusion culture) by allowing a liquid medium to pass through the damming while supplying the liquid medium to the inoculated cells.

In addition, the cell treatment container is also used, for example, for drug screening for the observation of the reaction of cells to a drug by allowing the drug to pass through a damming while supplying the drug to the cells that have been dammed up and inoculated in the damming.

SUMMARY

In the cell treatment container described in Helene Andersson et al., "MICROMACHINED FLOW-THROUGH FILTER-CHAMBER FOR SOLID PHASE DNA ANALYSIS", Micro Total Analysis Systems 2000, p. 473-476, it is conceivable to increase a flow volume of a cell suspension in order to rapidly perform the inoculation of cells. However, in the cell treatment container, if the flow volume is large, deformation may occur and the interval between pillars may be increased. This problem is particularly noticeable when the cell treatment container is made of a relatively soft material such as an elastomer.

The present invention has been made in view of such a circumstance, and an object of the present invention to provide a cell treatment container and a cell treatment device, which are suitable for cell inoculation.

A first aspect of the present invention relates to a cell treatment container, including: a first member having a flow path in which a cell suspension including a liquid and cells dispersed in the liquid flows through, the flow path formed on a surface of the first member; a second member arranged to face the surface of the first member; and a damming formed in one or both of the first member and the second member, in which the damming is provided with a protrusion part protruding from the first member into the flow path to form a gap for allowing the liquid in the cell suspension to pass through the gap and for damming up the cells in the cell suspension, and a pillar extending from the protrusion part at a first end and being joined to the second member at a second end.

A second aspect of the present invention relates to a cell treatment device, including: the cell treatment container according to the first aspect; and a first pump connected to an inlet port for the cell suspension.

According to the first aspect of the present invention, in a damming, a protrusion part dams up cells in a cell suspension, and a gap allows a liquid to pass through the gap, and therefore, conventional pillars are not required, and with a simple structure, the cell treatment container becomes suitable for mass production, and also suitable for use in application of drug screening or the like.

Further, since the damming is provided with a pillar extending from the protrusion part and to be joined to a second member, even if the protrusion part and the second member are firmly joined and fluid pressure is applied to the protrusion part, deformation of the damming (expansion in the gap) can be prevented.

According to the second aspect of the present invention, a first pump is connected to an inlet port for a cell suspension, and therefore, a cell suspension can be stably fed to a flow path of the cell treatment container.

DETAILED DESCRIPTION

[Configuration of Cell Treatment Container]

Hereinafter, an embodiment of the present invention will be described while making reference to drawings.

Figure 1:
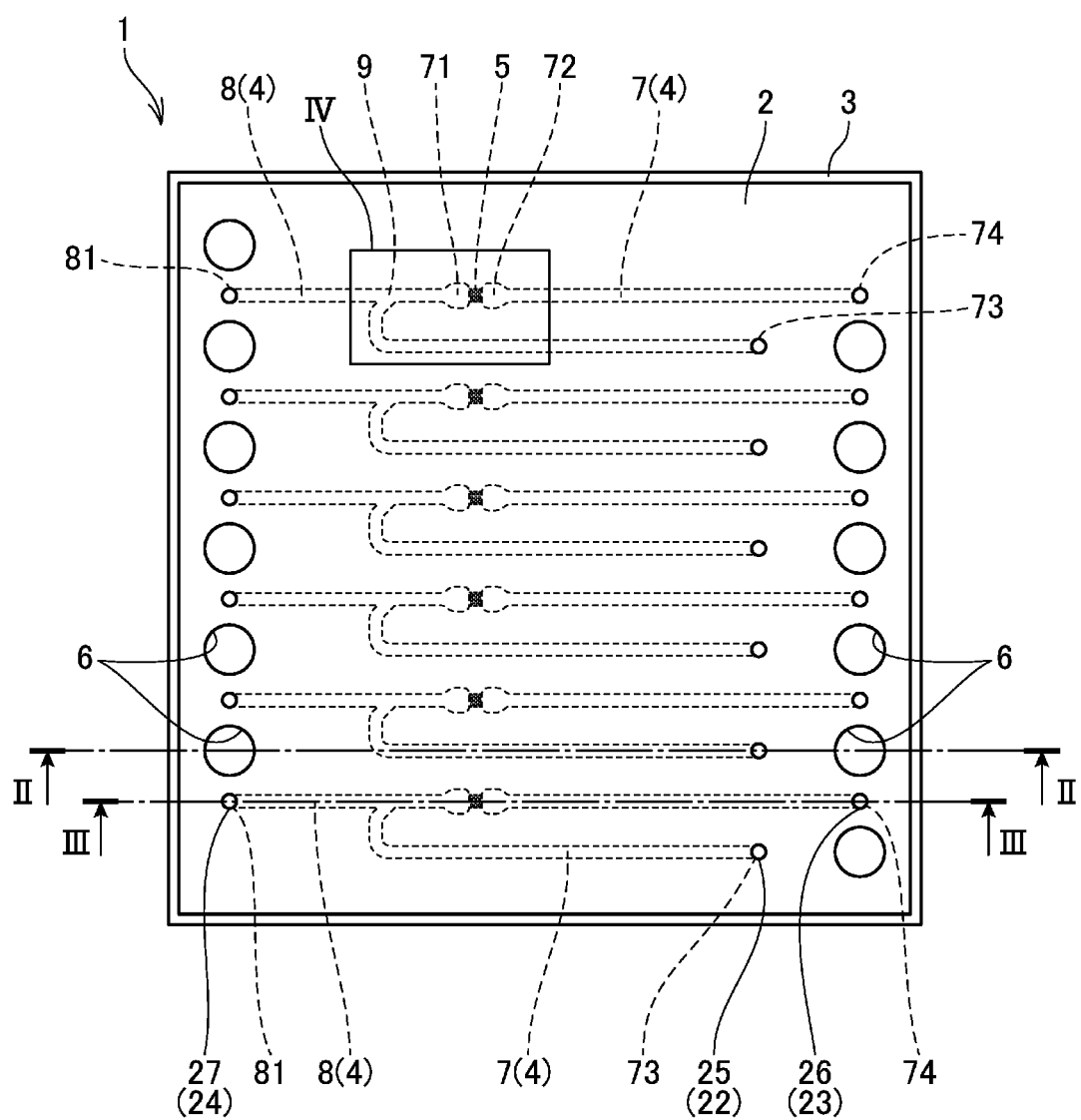
FIG. 1 is a plan view showing a cell treatment container according to an embodiment of the present invention.
Figure 2:
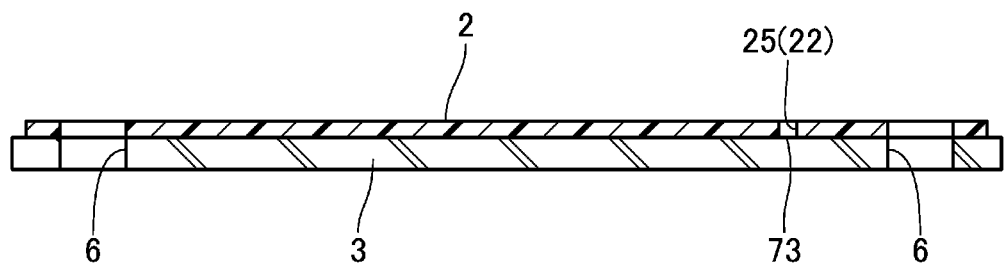
FIG. 2 is a II-II sectional view of FIG. 1.
Figure 3:
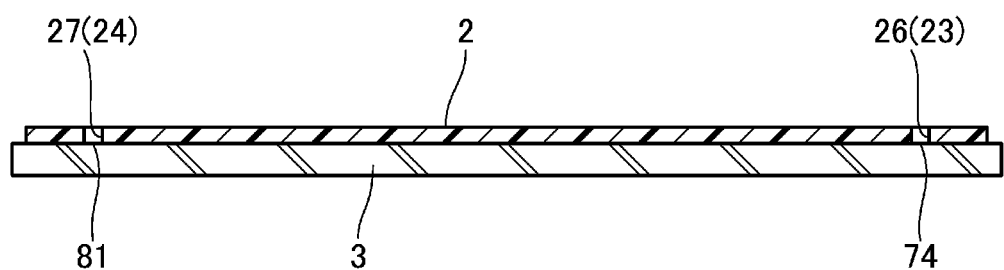
FIG. 3 is a III-III sectional view of FIG. 1.
Figure 4:
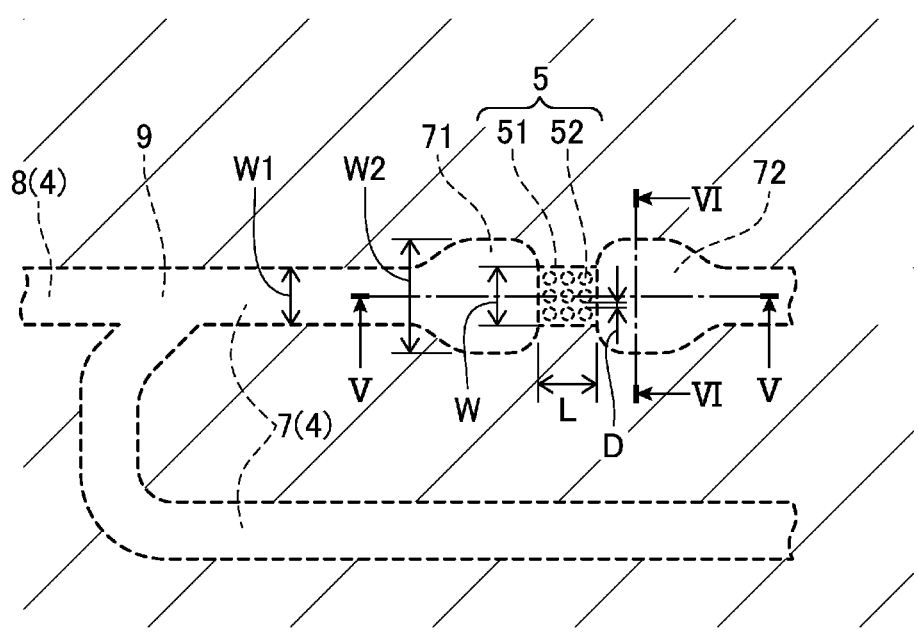
FIG. 4 is an enlarged view of a portion surrounded by a square IV in FIG. 1.

FIG. 1 is a plan view showing a cell treatment container according to the present embodiment. FIG. 2 is a II-II sectional view of FIG. 1. FIG. 3 is a III-III sectional view of FIG. 1. FIG. 4 is an enlarged view of a portion surrounded by a square IV in FIG. 1.

As shown in FIGS. 1 to 3, the cell treatment container 1 according to the present embodiment is a cell treatment container in which two flat plate-shaped members (a first member 2 and a second member 3) are joined to each other in a stacked state, and multiple sets (six sets in this embodiment) of flow paths 4 (see FIG. 1) are formed side by side on a joint surface (surface facing the second member 3) of the first member 2 with the second member 3.

In the present embodiment, the expression "cell treatment" is referred to as treatment of cell culture, cell evaluation, or the like, but is not limited thereto.

The first member 2 is made of colorless and transparent polydimethylsiloxane (PDMS), and is suitable for microscopic observation. The thickness of the first member 2 is not particularly limited, but is set to around 0.5 to 3 mm.

The second member 3 is a glass substrate made of colorless and transparent glass, and is suitable for microscopic observation. The thickness of the second member 3 is not particularly limited, but is set to, for example, around 1 to 6 mm.

The first member 2 made of PDMS is directly joined to the second member 3 made of glass by being pressed against the second member 3, but may be joined with an adhesive therebetween.

The flow path 4 is formed in the first member 2 made of PDMS.

In the joint surface of the first member 2 with the second member 3 (shaded area in FIG. 4), grooves 21 (see FIG. 5) that form six sets of flow paths 4 are formed. The open surfaces of the grooves 21 are surrounded by the second member 3, and the six sets of flow paths 4 are formed on the joint surface of the first member 2 with the second member 3. The cross section perpendicular to the longitudinal direction of the flow path 4 is formed in a rectangular shape.

As shown in FIG. 1, the flow path 4 in each of the sets is provided with a first flowing section 7 in a substantially U-shape, and a second flowing section 8 in a linear shape, merging with the first flowing section 7 (branched out from the first flowing section 7).

As shown in FIG. 4, in the first flowing section 7, a damming 5 for cells is formed on the downstream side of a merging part 9 with the second flowing section 8. The first flowing section 7 is widened on the entry side and the exit side of the damming 5. The width W of the damming 5 is substantially equal to the width W1 of the first flowing section 7, and is narrower than the width W2 of each of widened parts 71 and 72 of the first flowing section 7.

As shown in FIGS. 1 to 3, in the first member 2, a through hole 22 that communicates the upstream end 73 of the first flowing section 7 with the outside of the cell treatment container 1 is formed in the thickness direction of the first member 2. Further, a through hole 23 that communicates the downstream end 74 with the outside of the cell treatment container 1 is formed in the thickness direction of the first member 2, and a through hole 24 that communicates the upstream end 81 of the second flowing section 8 with the outside of the cell treatment container 1 is similarly formed in the thickness direction of the first member 2.

The through hole 22 that communicates with the upstream end 73 of the first flowing section 7 is an inlet port (first inlet port) 25 for a cell suspension in which cells have been dispersed in a first liquid. The through hole 24 that communicates with the upstream end 81 of the second flowing section 8 is an inlet port (second inlet port) 27 for a second liquid such as a liquid medium, or a drug solution. The through hole 23 that communicates with the downstream end 74 of the first flowing section 7 is an outlet port 26 for the first liquid and the second liquid.

As shown in FIG. 1, the first member 2 is slightly smaller than the second member 3, and positions of the four corners of the first member 2 are located inside the second member 3 in the plan view. Further, on both sides (on the left and right sides in FIG. 1) of the cell treatment container 1, multiple through holes 6 (six holes on each side in FIG. 1) each penetrating both members 2 and 3 in the thickness direction are formed at regular intervals along both end edges.

The width W of the flow path 4 is not particularly limited, but is, for example, around 0.5 to 3 mm, and the width W2 of each of the widened parts 71 and 72 on the entry side and the exit side of the damming 5 is around twice the width W.

The height H (see FIG. 5) of the flow path 4 is not particularly limited, but is, for example, around 0.02 to 0.2 mm.

The diameter of each of the first inlet port 25, second inlet port 27 and outlet port 26 that communicate with the flow path 4 is around the width W of the flow path 4.

The damming 5 for cells will be described in more detail.

Figure 5:
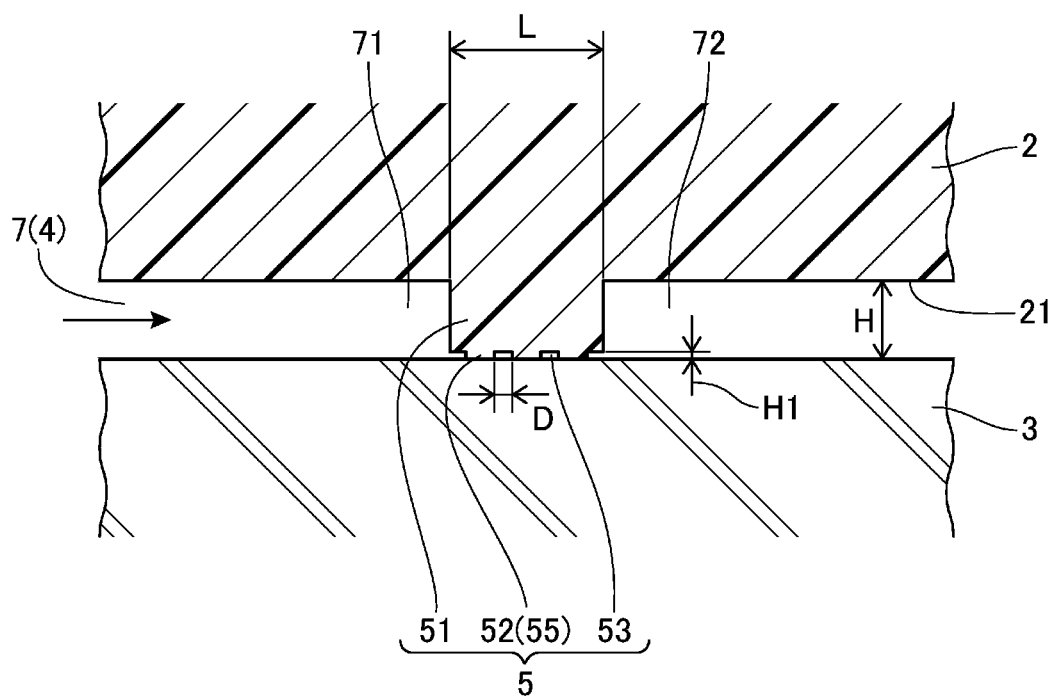
FIG. 5 is an enlarged view of a V-V sectional view of FIG. 4.

FIG. 5 is an enlarged view of a V-V sectional view of FIG. 4. In FIG. 5, the vertical direction is enlarged and illustrated as compared with the horizontal direction.

As shown in FIG. 5, the damming 5 is provided with a rectangular protrusion part 51 integrally formed with the first member 2, and a pillar part 52 integrally formed with the protrusion part 51 and joined to the second member 3. The protrusion part 51 and the pillar part 52 are formed on the first member 2 made of PDMS.

The protrusion part 51 is formed so as to block the first flowing section 7 in a state that a gap 53 with a height H1 is opened to the second member 3. As a matter of course, the height H1 of the gap 53 is set to be smaller than the diameter of the cells flowing through the first flowing section 7 and further to be a size with which the first liquid and the second liquid are allowed to pass through the gap 53.

The pillar part 52 has multiple (nine in the present embodiment) cylindrical bodies (pillars) 55 that are uniformly arranged on a surface of the protrusion part 51 and opposite to the second member 3.

As shown in FIGS. 4 and 5, the nine cylindrical bodies 55 are arranged in a direction of the liquid flow and also in a direction perpendicular to the liquid flow at substantially equal intervals D, between the adjacent cylindrical bodies 55. The size of this interval D does not depend on the diameter of the cell.

Figure 6:
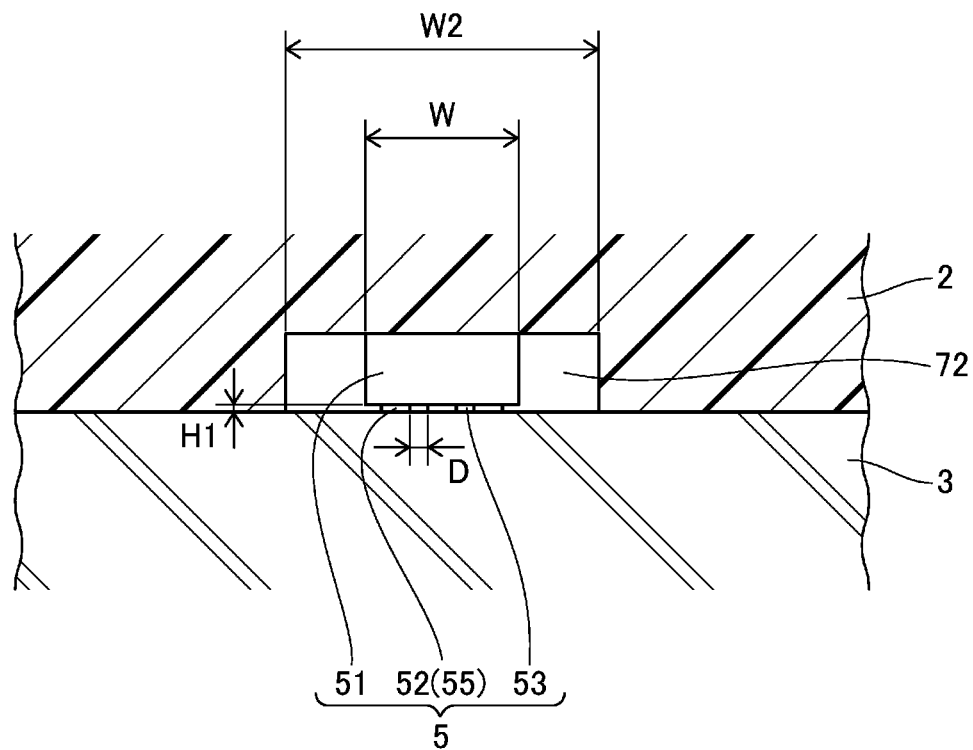
FIG. 6 is an enlarged view of a VI-VI sectional view of FIG. 4.

FIG. 6 is an enlarged view of a VI-VI sectional view of FIG. 4. In FIG. 6, the vertical direction is enlarged and illustrated as compared with the horizontal direction.

When the damming 5 is observed from the widened part 72 of the first flowing section 7, the damming 5 has a flow path width narrowed to the width W of the protrusion part 51, as shown in FIG. 6. In the gap 53 with a height H1 below the protrusion part 51, that is, between the protrusion part 51 and the second member 3, three cylindrical bodies 55 are observed.

The length L in the flow direction and the length (width) W in a direction perpendicular to the flow direction, of the protrusion part 51 are not particularly limited, but are set to, for example, around 0.5 to 3 mm.

The diameter of each of the cylindrical bodies 55 is set to, for example, around 0.1 to 0.6 mm, although it depends on the size of the protrusion part 51 and the number of the cylindrical bodies 55.

The formation pitch of the cylindrical bodies 55 is set to, for example, around 0.1 to 1 mm, although it depends on the size of the protrusion part 51 and the diameter of the cylindrical bodies 55.

[Configuration of Cell Treatment Device]

A cell treatment device using a cell treatment container 1 will be described.

Figure 7:
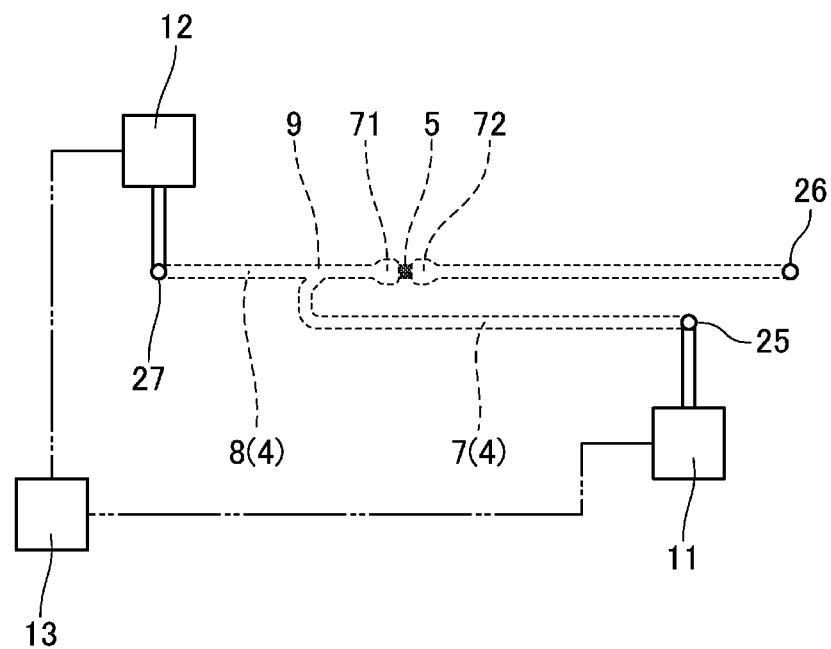
FIG. 7 is an illustration diagram schematically showing a cell treatment device according to an embodiment of the present invention.

FIG. 7 is an illustration diagram schematically showing a cell treatment device according to an embodiment.

As shown in FIG. 7, in the cell treatment device according to the present embodiment, for each of the sets of flow paths 4, a first pump 11 is connected to a first inlet port 25 with a tube or the like therebetween, and a second pump 12 is connected to a second inlet port 27 with a tube or the like therebetween. A drain (not shown) is connected to an outlet port 26. A control device 13 for controlling the operations of the first pump 11 and the second pump 12 is electrically connected to the first pump 11 and the second pump 12.

As the first pump 11 and the second pump 12, for example, a syringe pump, a peristaltic pump, or the like can be mentioned.

[Method for Treating Cells by Cell Treatment Device]

A method for treating cells by a cell treatment device will be described.

First, by using a first pump 11, a cell suspension is introduced from a first inlet port 25 into a first flowing section 7. As a result, cells flowing through the first flowing section 7 are dammed up in a protrusion part 51 (see FIG. 5) of a damming 5, and inoculated in a widened part 71 on the entry side of the damming 5. Further, a first liquid passes through a gap 53 (see FIG. 5) between the protrusion part 51 and a second member 3, and is discharged from an outlet port 26 to a drain.

Examples of the cells to be introduced include induced pluripotent stem (iPS) cells, and lesion cells.

The flow rate and flow volume of the cell suspension when the cells are inoculated are controlled with a control device 13, and the flow rate of the cell suspension is set to a high speed to the extent that the cells are not damaged. The control device 13 has a CPU (Central Processing Unit) (not illustrated) and a memory (not illustrated) that stores programs and various data, and controls the first pump 11 and the second pump 12 to control the flow rate and flow volume of the cell suspension by executing, by the CPU, the programs stored in the memory.

Next, in a case where the inoculated cells are subjected to perfusion culture, by using a second pump 12, a liquid medium is introduced from a second inlet port 27 into a second flowing section 8. As a result, the liquid medium flows from the second flowing section 8 to the first flowing section 7, passes through the gap 53 between the protrusion part 51 and the second member 3 while being supplied to the inoculated cells, and is discharged from an outlet port 26 to a drain through a widened part 72 on the exit side of the damming 5. The flow rate and flow volume of the liquid medium when the cells are subjected to perfusion culture are controlled with a control device 13, and the flow rate of the liquid medium is set to a lower speed as compared with the flow rate of the cell suspension when the cells are inoculated.

Since the cell treatment container 1 of the present embodiment has six sets of flow paths 4, six types at most of treatments can be performed on cells at the same time in one cell treatment container 1 by changing the kind of the cells to be introduced into the flow path 4 in each of the sets.

The first member 2 is made of PDMS, and therefore, has elasticity. For this reason, when pressure is applied to the protrusion part 51 of the damming 5 due to a flowing cell suspension or the like, the protrusion part 51 tends to deform in a direction in which the gap 53 between the protrusion part 51 and the second member 3 is expanded.

The present inventors, et al. have obtained the following findings through experiments.

Figure 8:
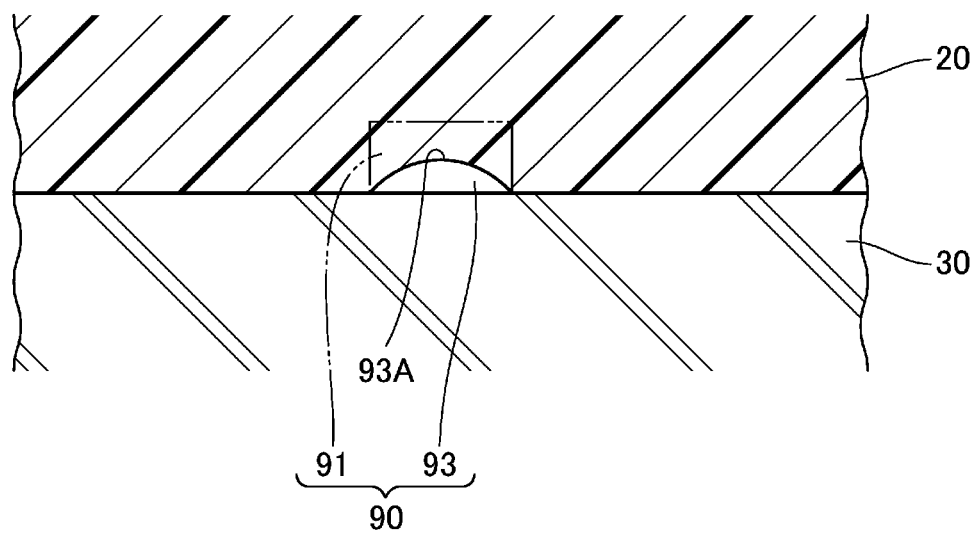
FIG. 8 is a reference diagram showing a comparative example of the cell treatment container.

FIG. 8 is a schematic reference diagram showing a part in which a first member 20 made of PDMS is joined to a second member 30 made of glass and a flow path is formed on a joint surface of the first member 20 with the second member 30.

In a case where a damming 90 is not provided with a pillar part 52 (see FIG. 6), it has been found that if a cell suspension is flowed at a flow rate at which cells are inoculated, since the first member 20 is made of PDMS, a gap 93 below a protrusion part 91 between the protrusion part 91 (shown by a dashed-two dotted line) and the second member 30 expands so as to push the central part 93A upward.

In contrast, as of the present embodiment, in a case where a pillar part 52 integrally formed with the protrusion part 51 is joined to the second member 3, even if a force for deforming the protrusion part 51 acts in a direction in which a gap 53 between the protrusion part 51 and the second member 3 is expanded due to the pressure of the flowing cell suspension, the expansion in the gap 53 can be prevented in advance.

[Effect]

As described above, the cell treatment container 1 of the present embodiment is suitable for cell inoculation, because in the damming 5, the protrusion part 51 dams up the cells in a cell suspension, and the gap 53 allows the liquid to pass through the gap 53.

Therefore, conventional pillars are not required, and with a simple structure, the cell treatment container 1 becomes suitable for mass production, and also suitable for use in application of drug screening or the like.

Further, PDMS as the material for the first member 2 is an inexpensive elastomer, and the glass substrate as the second member 3 is also a member that can be obtained inexpensively, and therefore, the production cost can be further suppressed.

In addition, if the material for the first member 2 is an elastomer such as PDMS, the damming 5 (protrusion part 51 and pillar part 52) can be easily formed integrally with the first member 2.

Further, if the second member 3 is a glass substrate, the second member 3 is hardly deformed in the gap 53 formed below the protrusion part 51, and the expansion in the gap 53 can be prevented.

Furthermore, since the protrusion part 51 is provided with the pillar part 52 that joins the first member 2 and the second member 3, the protrusion part 51 and the second member 3 are firmly joined, and even if a liquid passes through the gap 53 formed below the protrusion part 51, the deformation of the protrusion part 51 (expansion of the gap 53) can be prevented.

In addition, since the pillar part 52 has multiple cylindrical bodies (pillars) 55, the load applied to the protrusion part 51 can be dispersed in the multiple cylindrical bodies 55. Further, since the pillars are cylindrical bodies 55, the resistance when a liquid passes through between the multiple cylindrical bodies 55 can be reduced.

In addition, since the entry side of the damming 5 is widened, and the flow path width is suddenly narrowed in the damming 5, the flow rate of a liquid medium is suddenly decelerated in a widened part 71 so that the liquid medium is supplied to the entire inoculated cells.

Further, since the exit side of the damming 5 is widened, the liquid (first liquid and liquid medium) can easily pass through the damming 5. Furthermore, since the flow path width narrows in the downstream of a widened part 72, the flow rate of the liquid can be increased. With this arrangement, the reverse flow of the liquid can be prevented.

In addition, in the cell treatment device according to the present embodiment, a first pump 11 is connected to a first inlet port 25, and a second pump 12 is connected to a second inlet port 27, and therefore, a cell suspension and a liquid medium can be stably fed to a flow path 4.

[Other Embodiments]

In the embodiment described above, as the material for the first member 2, PDMS is used, however, any material can be used as long as it is colorless and transparent, and for example, silicone rubber or the like may be used. Even if such a material is used, a damming 5 can be easily formed integrally with a first member 2.

Further, in the embodiment described above, the material (PDMS) for the first member 2 is different from the material (glass) for a second member 3, however, the materials for both members 2 and 3 may be the same as each other. For example, as the material for each of both members 2 and 3, a material having elasticity such as PDMS, or silicone rubber is used, both members 2 and 3 can be easily formed. Moreover, even if such a material having elasticity is used, deformation of a protrusion part 51 (expansion of a gap 53) can be prevented by a pillar part 52.

In addition, in the embodiment described above, the damming 5 is formed in the first member 2, however, the damming 5 may be formed in the second member 3, or may be formed in both of the first member 2 and the second member 3.

Further, in the embodiment described above, a first flowing section 7 is made into a substantially U-shape and a second flowing section 8 is made into a linear shape, however, these shapes may be any other shapes, and for example, the first flowing section 7 may be made into a linear shape and the second flowing section 8 may be made into a substantially U-shape, or the like.

In addition, in the embodiment described above, six sets of flow paths 4 are formed in one cell treatment container 1, however, the number of the sets may be any other number or may be one.

Further, in the embodiment described above, as the treatment method for cells, the cells are subjected to perfusion culture, however, the cells may be treated by drug screening or the like. In a case of drug screening, a drug in place of the liquid medium is introduced from the second inlet port 27 into the second flowing section 8.

In addition, in the embodiment described above, as the inlet port of a liquid, a first inlet port 25 and a second inlet port 27 are provided, however, these inlet ports may be combined into one, and the flow path 4 may be one. In this case, a switching valve is connected to one inlet port, and a first pump 11 and a second pump 12 are connected to the switching valve. In this regard, the liquid to be introduced is switched by the switching valve.

Further, in the embodiment described above, a pillar part 52 is set to have multiple cylindrical bodies (pillars) 55, however, the number of pillars may be one. Furthermore, as the pillar, for example, a prismatic body, a plate body extending in a direction along the flow, or the like may be used in place of the cylindrical body 55.

In this regard, the embodiments described above are merely examples of aspects of the present invention, and can be arbitrarily modified and applied without departing from the gist of the present invention.

[Aspect]

It will be understood by those skilled in the art that the embodiments described above are specific examples of the following aspects.

(First item) A cell treatment container according to the first aspect may include: a first member having a flow path in which a cell suspension including a liquid and cells dispersed in the liquid flows through, the flow path formed on a surface of the first member; a second member arranged to face the surface of the first member; and a damming formed in one or both of the first member and the second member, in which the damming is provided with a protrusion part protruding from the first member into the flow path to form a gap for allowing the liquid in the cell suspension to pass through the gap and for damming up the cells in the cell suspension, and a pillar extending from the protrusion part at a first end and being joined to the second member at a second end.

According to the cell treatment container described in the first item, in the damming, the protrusion part dams up the cells in the cell suspension, and the gap allows the liquid to pass through the gap, and therefore, conventional pillars are not required, and with a simple structure, the cell treatment container becomes suitable for mass production, and also suitable for use in application of drug screening or the like.

Further, the damming is provided with a pillar extending from the protrusion part at a first end and being joined to the second member at a second end, and therefore, the protrusion part and the second member are firmly joined, and even if fluid pressure is applied to the protrusion part, deformation of the damming (expansion in the gap) can be prevented.

(Second item) In the cell treatment container described in the first item, the protrusion part may have a plurality of the pillars.

According to the cell treatment container described in the second item, the protrusion part has multiple pillars, and therefore, the load applied to the protrusion part can be dispersed in the multiple pillars.

(Third item) In the cell treatment container described in the first or second item, the first member may be made of an elastomer.

According to the cell treatment container described in the third item, the first member is made of an elastomer, and therefore, the effect described in the first item can be remarkably obtained. Further, the flow path, the protrusion part, and the pillars can be easily formed integrally.

(Fourth item) In the cell treatment container described in any one of the first to third items, a plurality of the flow paths are formed side by side in the first member, and the damming may be arranged in each of the flow paths.

According to the cell treatment container described in the fourth item, there are multiple flow paths, and therefore, multiple types of treatments can be performed on cells at the same time. In addition, multiple flow paths are formed side by side, and therefore, even if multiple flow paths are arranged, the cell treatment container can be made compact.

(Fifth item) In the cell treatment container described in any one of the first to fourth items, the second member may be a glass substrate.

According to the cell treatment container described in the fifth item, the second member is a glass substrate, and therefore, the second member can be prevented substantially from deforming in the gap formed below the protrusion part, and expansion in the gap formed below the protrusion part can be further prevented.

(Sixth item) In the cell treatment container described in any one of the first to fifth items, the flow path may include a first flowing section having an inlet port for the cell suspension, and a second flowing section being branched out from the first flowing section and having an inlet port for a liquid medium to be supplied to the damming through the first flowing section.

According to the cell treatment container described in the sixth item, the cell treatment container has a first flowing section having an inlet port for a cell suspension, and a second flowing section being branched out from the first flowing section and having an inlet port for a liquid medium, and therefore, it is easy to introduce a cell suspension into the first flowing section, and to introduce a liquid medium into the second flowing section.

(Seventh item) A cell treatment device according to the second aspect may include: the cell treatment container according to any one of the first to sixth items; and a first pump connected to the inlet port for the cell suspension.

According to the cell treatment device described in the seventh item, a first pump is connected to an inlet port for a cell suspension, and therefore, a cell suspension can be stably introduced into the inlet port.

(Eighth item) The cell treatment device described in the seventh item, may further include a second pump connected to the inlet port for the liquid medium.

According to the cell treatment device described in the eighth item, the second pump is connected to an inlet port for a liquid medium, and therefore, a liquid medium can be stably introduced into the inlet port.

(Ninth item) The cell treatment device described in the eighth item, may further include a control device for controlling operations of the first pump and the second pump, in which the control device may control the first pump and the second pump so that a flow volume of the cell suspension to be introduced into the first flowing section is larger than a flow volume of the liquid medium to be introduced into the second flowing section.

According to the cell treatment device described in the ninth item, the flow volume of a cell suspension fed from a first pump is controlled with a control device so as to be larger than the flow volume of a liquid medium fed from a second pump, and therefore, a liquid containing cells can be sent at a high speed during cell inoculation, and a liquid medium can be sent at a low speed during perfusion culture.

REFERENCE SIGNS LIST

1: Cell treatment container
2: First member
3: Second member
4: Flow path
5: Damming
7: First flowing section
8: Second flowing section
11: First pump
12: Second pump
13: Control device
51: Protrusion part
52: Pillar part
53: Gap
55: Cylindrical bodies

What is claimed is:

1. A cell treatment container, comprising:
a first member having a flow path in which a cell suspension including a liquid and cells dispersed in the liquid flows through, the flow path formed on a surface of the first member;
a second member arranged to face the surface of the first member; and
a damming formed in one or both of the first member and the second member, wherein
the damming is provided with:
a protrusion part protruding from the first member into the flow path to form a gap for allowing the liquid in the cell suspension to pass through the gap and for damming up the cells in the cell suspension, and
a pillar extending from the protrusion part at a first end and being joined to the second member at a second end.

2. The cell treatment container according to claim 1, wherein
the protrusion part has a plurality of the pillars.

3. The cell treatment container according to claim 1, wherein
the first member is made of an elastomer.

4. The cell treatment container according to claim 1, wherein
a plurality of the flow paths are formed side by side in the first member, and
the damming is arranged in each of the flow paths.

5. The cell treatment container according to claim 1, wherein
the second member is a glass substrate.

6. The cell treatment container according to claim 1, wherein
the flow path includes:
a first flowing section having an inlet port for the cell suspension, and
a second flowing section being branched out from the first flowing section and having an inlet port for a liquid medium to be supplied to the damming through the first flowing section.

7. A cell treatment device, comprising:
the cell treatment container according to claim 6; and
a first pump connected to an inlet port for the cell suspension.

8. The cell treatment device according to claim 7, further comprising
a second pump connected to the inlet port for the liquid medium.

9. The cell treatment device according to claim 8, further comprising
a control device for controlling operations of the first pump and the second pump, wherein
the control device is operable to control the first pump and the second pump so that a flow volume of the cell suspension to be introduced into the first flowing section is larger than a flow volume of the liquid medium to be introduced into the second flowing section.

* * * * *